United States Patent [19]

Tobiki et al.

[11] Patent Number: 5,336,469
[45] Date of Patent: Aug. 9, 1994

[54] REAGENT FEEDER

[75] Inventors: Hisao Tobiki; Hiroaki Matsushima, both of Takarazuka, Japan

[73] Assignee: Nihon Medi-Physics Co., Ltd., Nishinomiya, Japan

[21] Appl. No.: 863,962

[22] Filed: Apr. 6, 1992

[30] Foreign Application Priority Data

Apr. 15, 1991 [JP] Japan .................. 3-25025[U]

[51] Int. Cl.⁵ .............. B01L 3/02; B65H 3/00
[52] U.S. Cl. ................. 422/100; 221/266; 221/289; 141/352; 141/354
[58] Field of Search ............. 141/351–354, 141/362; 221/266, 289, 298, 299; 422/100

[56] References Cited

U.S. PATENT DOCUMENTS

| | | | |
|---|---|---|---|
| 3,269,597 | 8/1966 | Passavanti | 221/289 |
| 4,101,284 | 7/1978 | Difiglio et al. | 23/259 |
| 4,354,619 | 10/1982 | Wippermann et al. | 221/263 |
| 4,402,425 | 9/1983 | von Schuckmann | 221/202 |
| 4,937,048 | 6/1990 | Sakai et al. | 422/63 |
| 5,018,644 | 5/1991 | Hackmann et al. | 221/65 |
| 5,108,006 | 4/1992 | Tieke et al. | 221/152 |

FOREIGN PATENT DOCUMENTS

| | | |
|---|---|---|
| 0209994 | 6/1986 | European Pat. Off. . |
| 3417751 | 4/1987 | European Pat. Off. . |
| 2641764 | 7/1990 | France . |
| 2643881 | 9/1990 | France . |
| 61-6446 | 2/1986 | Japan . |
| 1191834 | 5/1970 | United Kingdom . |

OTHER PUBLICATIONS

European Search Report-EP 92 1066069.

Primary Examiner—James C. Housel
Assistant Examiner—Milton I. Cano
Attorney, Agent, or Firm—Jones, Tullar & Cooper

[57] ABSTRACT

A reagent feeder which can to be used in both a finger-push system and a slide system by only attaching and detaching a simple auxiliary component to and from a case body depending on the state of operation or a preference of the operator. The feeder includes a case body, a sphere discharge port and a discharge device, so as to discharge a sphere one by one by pushing down the discharge device. The discharge device is provided with an operation lever which extends out of the case body and can be pushed down by a finger. A slide cover surrounding an outer periphery of the case body is attached to the case body in such a way that it can be moved freely in a vertical direction and can be detached from the case body. The slide cover is engaged with the operation lever of the discharge device so that it can be moved integrally with the discharge device.

5 Claims, 3 Drawing Sheets

Lower side

REAGENT FEEDER

BACKGROUND OF THE INVENTION

1. Field of the Invention

This invention relates to a reagent feeder for charging a fixed quantity of reagent into a specimen such as blood or urine collected in a test tube etc., and particularly to a reagent feeder appropriate for charging a fixed quantity of reagent into a number of specimens in order respectively.

2. Discussion of Prior Art

In the case when reagents are charged into a number of specimens of fixed quantity and inspected respectively, it is required that the quantity of reagent in each test tube must be uniform in order to get exact inspection results. It is extremely difficult to supply a very small and fixed quantity of reagent in every test tube by using a pipet etc., so that exact inspection results can not be expected.

In order to cope with the above-mentioned requirement, there have been developed various reagent feeders accomplishing the exact feeding of a fixed quantity of reagent, in which the fixed quantity of reagent is forced to adhere to a sphere made of synthetic resin etc. having a definite standard. Many of the spheres are housed in a case, so that the sphere is charged in each specimen one by one. For example, there are disclosed Published Patent Application (KOKAI) No 62-24147 and Japanese Examined Utility Model Application (KOKOKU) No. 61-6446 etc.

Operation is simple in the finger-push system disclosed in the first noted prior art. In the case of a great number of specimens, however, the operator's fingers become extremely fatigued so that continuous operation becomes impossible, because the operation load is concentrated on his fingers. In the case-slide system disclosed in the later noted prior art, the operator's fingers will be less fatigued and the system is apt to be well-adapted to operation of the great many number of specimens because the entire case is gripped by his hand. However, since the lower end discharge port is pushed upon a port of a test tube etc., the operation will sometimes become difficult when the test tube etc. is installed in an unstable position.

Which system is excellent can not be decided unconditionally as described above, because the suitability of each discharge system differs depending on the number of specimens or the state of the test tube etc. in which the specimen is put, or a preference of operator. Therefore, it is preferable to prepare all of the above reagent feeders and select a most suited reagent feeder from them as occasion demands. However, this way is uneconomical because of the great waste in cost and control.

An object of the invention is to provide a reagent feeder which can be used as both a finger-push system and a slide system by only attaching and detaching a simple auxiliary component to and from a case body depending on a state of operation or an operator preference.

SUMMARY OF THE INVENTION

In order to solve the above problem, this invention provides a reagent feeder comprising a case body housing plural spheres to which reagents adhere, a sphere discharge port formed at a bottom portion of the case body, and a discharge device supported in the case body freely movably in a vertical direction and urged to an upper waiting position by elastic means, the discharge device stopping a sphere situated at a position immediately before the discharge port, releasing the stopped state of the sphere to discharge only the above-mentioned sphere to the discharge port when the discharge device is pushed downward, and sending out the next sphere to the position immediately before the discharge port when the discharge device is returned to the upper waiting position; characterized in that an operation lever which extends out of the case body to allow for finger push-down operation, is formed on the discharge device, a slide cover surrounding an outer periphery of the case body is attached to the case body in such a way that it can be moved freely in the vertical direction and can be detached from the case body, and the slide cover is engaged with the operation lever of the discharge device so that it can be moved integrally with the discharge device.

When the feeder is to be used in the finger-push system, the slide cover should be removed from the case body. That is; the case body is gripped, and the lower end discharge port is brought to a port position of a test tube etc., the operation lever is pushed down by a finger. Thus, one sphere to which the reagent adheres can be charged in the test tube. When the feeder is to be used in the slide system, the slide cover is attached to the case body and simultaneously engaged with the operation lever. That is; the slide cover is gripped, the lower end discharge port is pressed against the port of test tube etc., and the slide cover is pushed down. Thus, one sphere to which the reagent adheres can be charged in the test tube.

As described above, the present invention includes the following advantages:

(1) In the reagent feeder for feeding the sphere to which a fixed quantity of reagent adheres to each specimen one by one, the finger operated operation lever is installed thereon as a means for operating the discharge device to send and discharge the reagent one by one, and the slide cover which engages with the operation lever so as to move together with the operation lever, is attached to the case body in a freely attachable and detachable way. Therefore, the feeder can be easily changed to a discharge system suitable for respective conditions by only attaching or detaching the slide cover according to the quantity of specimen, the installation stability of test tube etc. or operator preference, so that the practical effect of the feeder is great.

(2) Since the case can be used as it is when the application mode is changed between the finger-push system and the slide system, it becomes unnecessary to prepare for all types of reagent feeders so that the feeder of the present invention is preferable from the standpoint of cost and control.

DESCRIPTION OF THE PREFERRED EMBODIMENTS

Figure 4:
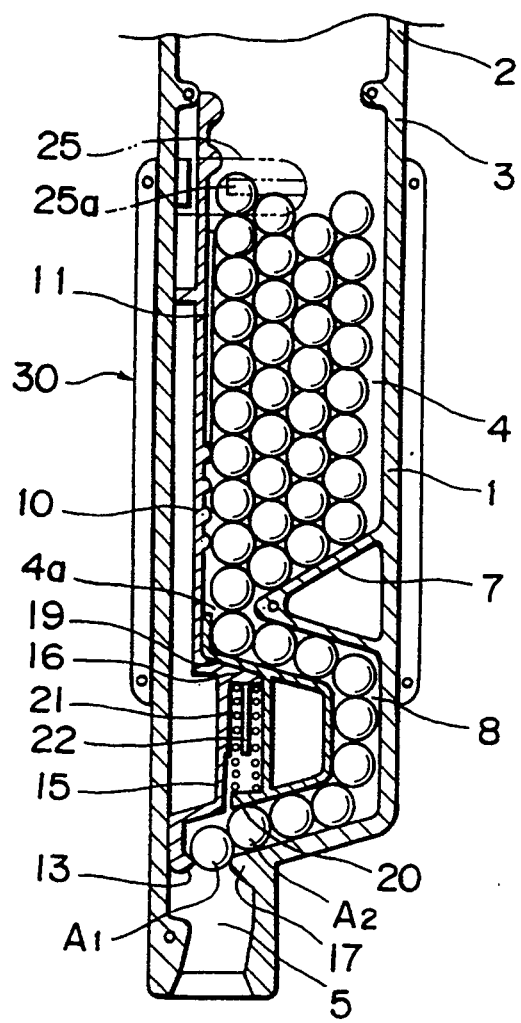
FIG. 4 is an enlarged sectional view taken along line IV—IV of FIG. 2.
Figure 5:
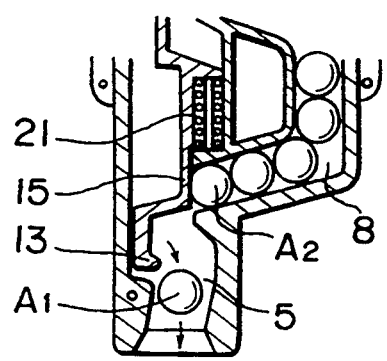
FIG. 5 is a partial sectional view showing a state where a sphere is discharged.
Figure 6:
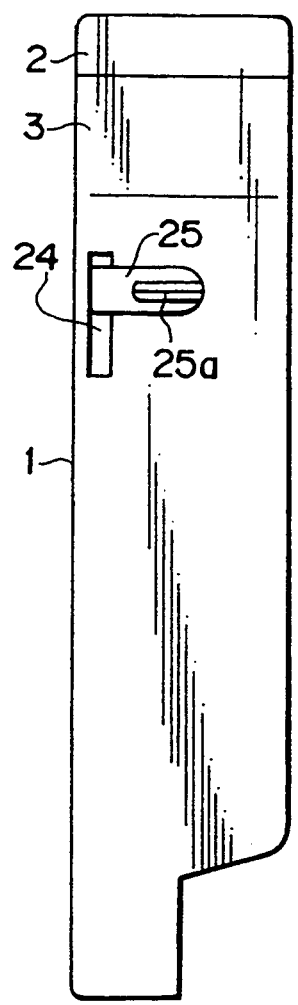
FIG. 6 is a front view of a state where a slide cover is removed.
Figure 7:
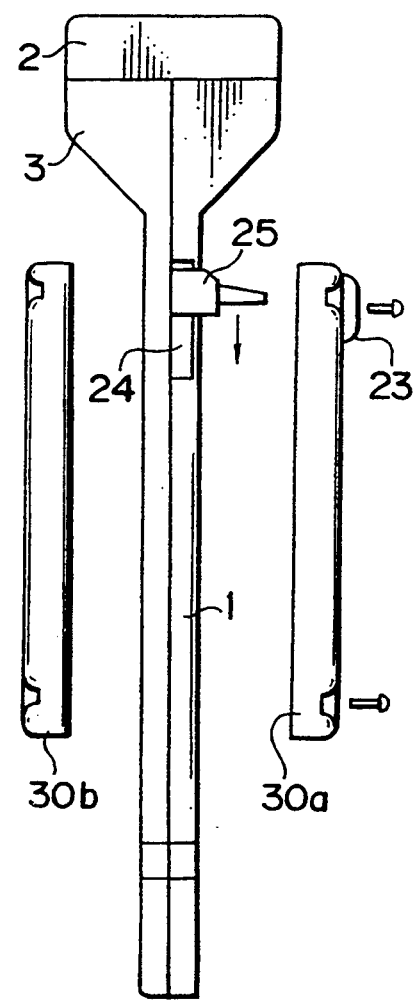
FIG. 7 is a side view of a state where a slide cover is removed.

FIG. 1 through FIG. 7 show an example of the reagent feeder according to the present invention. FIG. 1 through FIG. 5 show the state where the feeder is used in the slide system, and FIG. 6 and FIG. 7 show the state where the feeder is used in the finger-push system. In FIG. 6 and FIG. 7, a case body 1 is shown which is made of transparent synthetic resin etc. and is formed into a vertically long and flat box-shape. The case body, has integrally a cylindrical hopper 3 on its upper portion. A cover 2 is placed on top of the hopper 3 to be freely attachable and detachable. An operation lever 25 movable in the vertical direction extends from inside of the case body 1 to its surface side, and a tongue 25a for pushing down the operation lever 25 is formed integrally on it.

Referring to FIG. 4, the case body 1 is shown to have a sphere housing chamber 4 at a lower portion of the hopper 3 and includes a downward opening discharge port 5 at a left end in the figure on its bottom end. A bottom wall 7 of the sphere housing chamber 4 inclines downward to its left side and the chamber includes a connecting port 4a at its left bottom end. A lateral-trapezoidal or snaking sphere guide passage 8 is formed between the connecting port 4a and the discharge port 5, the sphere guide passage 8 has a sectional area for drawing up the spheres in line and for passing them, and a projection 17 for stopping a sphere A1 is integrally formed on a terminal portion of the guide passage.

A discharge device 10 for releasing the pheres one by one is formed long in the vertical direction and arranged freely movably in the vertical direction along a left wall surface in the case body 1, and a bottom edge of the discharge device 10 comes up to an upper end of the discharge port 5. An engaging projection 13 fronting on the lower end projection 17 of the sphere guide passage 8 is formed thereat, and a sphere A1 situated at a position immediately before the discharge port is stopped by both projections 13 and 17.

A shutter surface 15 is formed on an upper part of the projection 13 through an L-shaped portion, and the shutter surface 15 comes into and withdraws from the terminal portion of the guide passage 8 according to a vertical movement of the discharge port 10 so as to open and close the terminal portion of the guide passage 8. A spring receiver 16 is integrally formed on an upper portion of the shutter surface 15, and a return spring 21 is compressedly installed between the spring receiver 16 and a case body 1 side lower spring receiver 20. The return spring 21 urges the discharge device 10 upward, and the discharge device 10 is held at a waiting position shown by FIG. 4 when the spring receiver 16 comes in contact with a case-body side stopper 19. 22 denotes a guide pin.

As described above, the operation lever 25 formed integrally on the upper end of the discharge device 10 extends to the case body surface side passing through a guide lever hole 24 of the case body 1. The lever is bent to a central side of the case body and integrally has the foregoing tongue 25a at its tip end.

Figure 3:
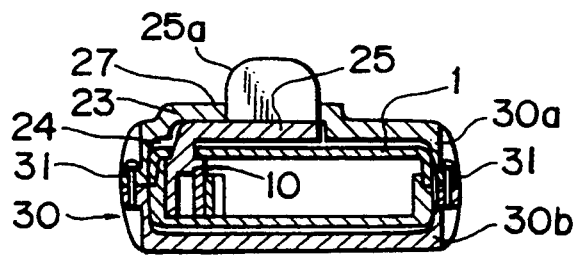
FIG. 3 is an enlarged sectional view taken along the line III—III of FIG. 1.

In FIG. 3, a slide cover 30 for changing from the finger-push system to the slide system is made of transparent synthetic resin and has a two-block construction including a front cover member 30a and a rear cover member 30b. Both cover members 30a and 30b have a flat U-shaped cross section. Both cover members 30a and 30b are mated to each other at their opening edges and connected together by screws 31 at four corners, so as to be formed into a cylindrical shape having a rectangular cross section. Thereby, the cover can encase an outer periphery of the case body 1 in such a manner as to be freely attachable and detachable and freely movable in the vertical direction. A convex portion 23 able to house the operation lever 25 is formed on the front cover member 30a, an engaging hole 27 with which the tongue 25a of the operation lever 25 engages is formed on the convex portion 23, and the slide cover 30 can be moved together with the discharge device 10 in the vertical direction when the tongue 25a engages with the engaging hole 27.

The function will be described hereafter.

In order to use the feeder in the finger-push system, the slide cover 30 should be disassembled and removed from the case body 1, as, previously as illustrated in FIG. 7. Naturally, plenty of spheres should be housed in the case body 1 from the upper hopper 3. Under this state, the case body 1 is gripped, the discharge port 5 is brought to the position of a test tube port etc., and the tongue 25a of the operation lever 25 is pushed down. Then, the entire discharge device 10 of FIG. 4 comes down against the return spring 21, so that the sphere A1 stopped by the projection 13 is released and discharged into the test tube from the discharge port 5 as shown by FIG. 5. At the same time, the shutter surface 15 closes the terminal portion of the guide passage 8 to prevent the next sphere A2 from moving to the upper end of the discharge port 5. After completion of supplying the sphere, the discharge device 10 is lifted up by the return spring 21 when the finger is released from the tongue 25a. Thereby, the shutter surface 15 opens the guide passage 8, and the next sphere A2 is fed to the projections 13 and 17 so as to return to the same state as FIG. 4.

Figure 1:
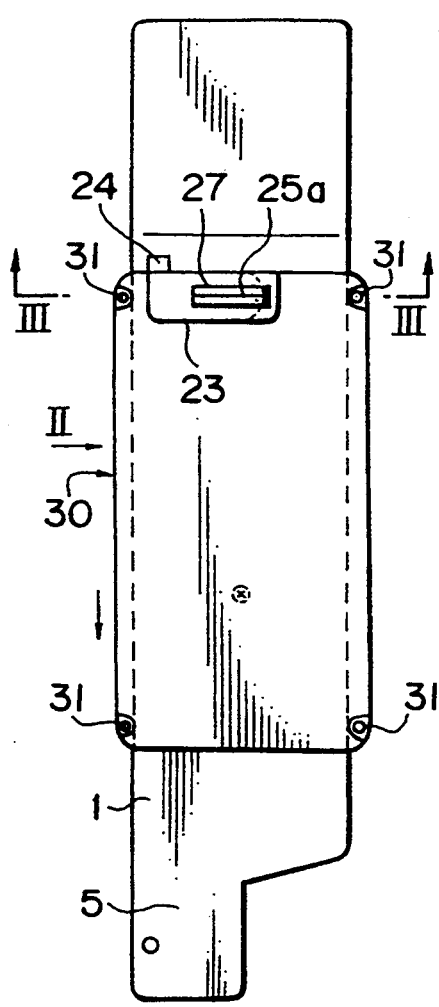
FIG. 1 is a front view of the reagent feeder according to the present invention.
Figure 2:
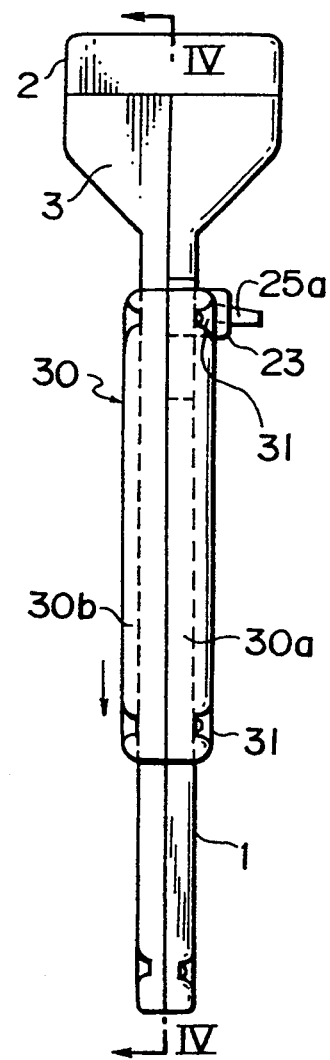
FIG. 2 is a side view (viewed in the direction of arrow II) of FIG. 1.

In order to use the feeder in the slide system, the slide cover members 30a and 30b should be put on the case body 1 from both front and rear sides as illustrated in FIG. 1 and FIG. 2, the tongue 25a of the operation lever 25 should be engaged with the engaging hole 27 of the front cover member 30a, and both members 30a and 30b should be fastened by plural screws 31. When using the feeder, the slide cover 30 is gripped by hand, the lower edge of the discharge port 5 is pressed upon the upper end of the test tube etc., and the discharge device 10 is pressed down by pushing down the slide cover 30 itself relative to the case body 1. Thereby, one sphere can be released as shown by FIG. 5, and the state of FIG. 4 is restored by returning the slide cover 30 upward.

Figure 8:
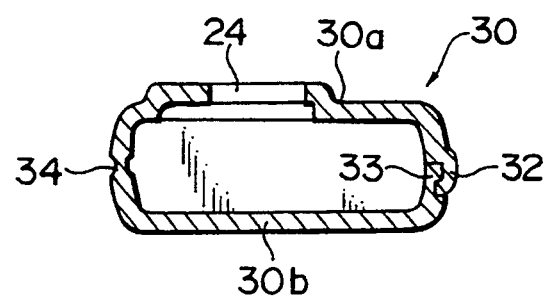
FIG. 8 is a sectional view showing another embodiment of the slide cover.

FIG. 8 shows another embodiment of the slide cover 30. A pair of cover members 30a and 30b are formed integrally so as to be freely opened and closed through a hinge 34, and are so constructed that they can be closed into a box-shape by means of a stopper mechanism composed of a projection 33 and a concave portion 32.

What is claimed is:

1. A reagent feeder, comprising: a case body having a slot at an upper end formed in a side wall thereof and a bottom portion defining a sphere discharge port at the other end; a discharge means supported in the case body to be freely movable in a vertical direction; elastic means for urging the discharge means and the case body defining a chamber housing a plurality of spheres to each of which a reagent adheres, the discharge means being adapted to stop at least one sphere situated at a position immediately before the discharge port, release the stopped sphere, thereby discharging said stopped sphere to the discharge port when the discharge means is pushed downward from said upper waiting position, and receive the next sphere to the position immediately before the discharge port when the discharge means is returned to said upper waiting position; an operating lever extending outwardly from the slot in the side wall of the case body to allow a finger operated pushdown operation of the discharge means, the operation lever being formed as part of the discharge means; and a pipe-shaped slide cover open at both ends, the slide cover being connected to and surrounding an outer periphery of the case body in such a way that the slide cover can be moved freely in the vertical direction and can be detached from the case body, the slide cover being engaged with the operation lever so as to be moved integrally with the discharge means.

2. A reagent feeder as set forth in claim 1, in which the case body and the slide cover are made of transparent synthetic resin.

3. A reagent feeder as set forth in claim 1 or claim 2, in which the slide cover is formed into a two-block construction comprising a front side cover member and a rear side cover member.

4. A reagent feeder as set forth in claim 3, in which the both cover members are formed integrally so as to be opened and closed through a hinge and can be closed by means of a stopper mechanism.

5. A reagent feeder as set forth in claim 2, in which the slide cover is formed into a two-block construction comprising a front side cover member and a rear side cover member.

* * * * *